United States Patent [19]

Shiba

[11] 4,218,435

[45] * Aug. 19, 1980

[54] COMPOSITION FOR PERMANENT WAVING

[75] Inventor: Kikuo Shiba, Tokyo, Japan

[73] Assignee: Yamanouchi Pharmaceutical Co., Inc., Tokyo, Japan

[*] Notice: The portion of the term of this patent subsequent to May 8, 1996, has been disclaimed.

[21] Appl. No.: 971,415

[22] Filed: Dec. 20, 1978

Related U.S. Application Data

[63] Continuation of Ser. No. 822,717, Aug. 8, 1977, Pat. No. 4,153,681.

[30] Foreign Application Priority Data

Aug. 19, 1976 [JP] Japan ................................. 51-98897

[51] Int. Cl.² ............................................... A61K 7/09

[52] U.S. Cl. ........................................ 424/72; 424/71
[58] Field of Search .................................. 424/70, 72

[56] References Cited

U.S. PATENT DOCUMENTS 2,405,166  8/1946  Reed et al. ............................ 424/72

OTHER PUBLICATIONS

Chemical Abstracts, vol. 68 (1968), p. 58384y.
Chemical Abstracts, vol. 78 (1973), p. 102007k.
Chemical Abstracts, vol. 77 (1972), p. 84685c.

*Primary Examiner*—V. D. Turner
*Attorney, Agent, or Firm*—Burgess, Ryan and Wayne

[57] ABSTRACT

A composition for permanent waving of hair comprising an aqueous solution containing the lower alkyl ester of cysteine or a salt thereof as the main ingredient and having a pH of 6.0–10.0.

9 Claims, No Drawings

COMPOSITION FOR PERMANENT WAVING

CROSS-REFERENCE TO RELATED APPLICATION

This application is a continuation of co-pending application Ser. No. 822,717, filed Aug. 8, 1977, now U.S. Pat. No. 4,153,681.

DETAILED EXPLANATION OF THE INVENTION

The invention relates to a novel composition for permanent waving of hair. More particularly, the invention relates to a composition for permanent waving of hair containing a cysteine derivative as the main ingredient and still more particularly it relates to a composition for permanent waving of hair comprising an aqueous solution containing the lower alkyl ester of cysteine or a salt thereof as the main ingredient and having a pH of 6.0–10.0.

The most common composition for permanent waving contains thioglycolic acid or a salt thereof as the main ingredient but it is known that due to its strong activity to hair, the composition sometimes causes discoloring, cutting, falling, branching, etc., of the hair as well as such troubles as inflammation, discoloration, etc., of skin.

Recently, for overcoming the aforesaid faults cysteine which is one of the sulfur-containing amino acids is used as the main ingredient of a composition for permanent waving of hair in place of thioglycolic acid or a salt thereof. As the cysteine is a component found in the human body, in particular human hair, the activity to the hair and skin is mild and hence does not cause troubles as encountered in the case of using a composition containing thioglycolic acid or a salt. However, since cysteine is liable to be oxidized and is hence unstable, the composition for permanent waving containing cysteine as the main ingredient has such faults that the reducing power of the composition is greatly decreased during the preservation of it, which results in reducing the waving effect. Furthermore, a cysteine-containing permanent waving composition is also accompanied by such faults that during the permanent waving of hair, the water-insoluble crystals of cystine which is the oxidation product of cysteine are formed and attached onto the hair, head skin, comb, etc., which gives an unpleasant feeling and spoils the finished beauty. The removal of the crystals requires a very troublesome treatment since it is not easy to remove the crystals by water washing.

Also, the specifications of British Pat. No. 1,002,889 discloses a composition for permanent waving containing the N-acyl derivative of cysteine such as, for example N-acetylcysteine as the main ingredient but in the case of using the composition, it is possible to effect the permanent waving under only an alkaline condition, in particular at a pH above 9, and the effect of permanent waving is insufficient.

As the result of various investigations, the inventor has discovered that a composition for permanent waving of hair containing the lower alkyl ester of cysteine shown by the formula

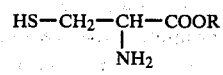

wherein R represents a lower alkyl group, and a mineral acid salt thereof, preferably cysteine methyl ester and a mineral acid salt thereof has mild activity to hair and skin, can be stably preserved for a long period, causes no deposition of undesirable crystals as encountered in the case of using cysteine, and provides a natural wave of hair having natural luster and full pliability.

The composition for permanent waving of this invention can be used at a pH of 6.0–10.0, in particular it can be conveniently used at a pH of 6.5–7.5.

The common compositions for permanent waving are ineffective at a pH range of 6.0–7.5 and are mainly used at an alkaline condition of pH 8–10, while the composition for permanent waving of this invention can be conveniently used under the condition of pH 6.5–7.5.

Since the skin surface of the human body is in weak acidic condition in the most natural state, the composition for permanent waving of this invention does not irritate the skin and does not cause other skin problems.

The composition for permanent waving of this invention is prepared as a 3–10% aqueous solution of, for example, the hydrochloride of cysteine methyl ester and in this case, the pH of the aqueous solution is adjusted to 6.0–10.0, preferably 6.5–7.5 with an inorganic base or an organic base. Examples of the inorganic base are an alkali hydroxide, an alkali carbonate, ammonia, etc., and examples of the organic base are monoethanolamine, diethanolamine, ethylenediamine, piperidine, etc.

Moreover, the hair-waving composition of this invention may further contain proper amounts of a suitable emulsifier (such as cholesterol, polyethyleneglycol higher alcohol ether, polyethyleneglycol higher fatty acid ester, etc.,); a penetrant (such as, palmitic acid isopropyl ester, myristic acid isopropyl ester, etc.,); a wetting agent (such as cetyl alcohol, polyethylene glycol, glycerol, etc.,); an anti-histaminic agent (such as diphenhydramine hydrochloride, etc.,); a viscosity-increasing agent (such as sodium alginate, carboxymethyl cellulose, polyvinyl alcohol, etc.,); a stabilizing agent (such as ethylenediaminetetraacetate, etc.,); a perfume; a coloring agent; and the like.

The composition for permanent waving of this invention can be used in a cold system, a hot system, curling iron, etc., in a beauty salon and is also very suitable for domestic use, since the composition shows a mild activity to hair and skin and the hair can be easily washed with water after the application of permanent waving by the composition.

The invention will be further explained in detail by the following examples.

EXAMPLES 1–10

In 100 ml of water was dissolved 10 g of cystein methyl ester hydrochloride and then the pH of the aqueous solution thus prepared was adjusted to the value as shown in Table 1 with sodium carbonate. A tress of hair which had not been given a permanent wave, was washed well with a cleaner and dried. And then, the tress was rolled on a curling iron and immersed in the aqueous solution prepared above for 25 minutes at 25° C., washed with water and dried. The permanent waving effect obtained was observed and the result was also compared with the case of treating tresses of hair with cysteine or N-acetylcysteine in a similar manner, the results being shown in Table 1. (In the table, the increase of the number of mark "+" means the increase of the permanent waving effect).

Table 1

| Example No. | pH | Permanent waving effect | | |
|---|---|---|---|---|
| | | Cysteine Methylester | Cysteine | N-Acetyl-Cysteine |
| 1 | 5.0 | ++ | — | — |
| 2 | 6.0 | +++ | — | — |
| 3 | 6.5 | ++++ | + | — |
| 4 | 6.8 | +++++ | ++ | — |
| 5 | 7.0 | +++++ | ++ | — |
| 6 | 7.7 | ++++ | +++ | — |
| 7 | 8.5 | +++ | ++++ | — |
| 8 | 8.0 | +++ | +++++ | — |
| 9 | 10.3 | +++ | +++++ | + |
| 10 | 10.7 | +++ | ++++ | — |

EXAMPLE 11

In 70 ml of water was dissolved 10 g of cysteine methyl ester hydrochloride and after adjusting the pH of the solution to 6.5 by the addition of 2.4 g of sodium carbonate, 1.5 g. of Emacol O (a trade name, make by Sanei Kasei K.K., consisting of 34% by weight paraffin oil, 8% by weight polyoxyethylene oleyl ether (10 E. O.), 6% by weight sorbitan trioleate, 2% by weight polyoxyethylene sorbitan monooleate, and 50% by weight of purified water), 0.7 g. of polyethylene glycol 4,000, 0.05 g. of diphenhydramine hydrochloride, and 0.03 g. of ethylenediamine tetraacetate were added to the solution followed by stirring to dissolve these additives. Then, after adding to the resultant solution a proper amount of a perfume, water was added to make the whole volume 100 ml. Thereafter, the pH of the solution was adjusted to 7.0 by the addition of 1.5 g of sodium carbonate to provide the hair-waving composition.

What is claimed is:

1. A composition for permanent waving of hair consisting essentially of an aqueous solution of a lower alkyl ester of cysteine or a mineral acid salt thereof and having a pH of 6.0–10.0, wherein the proportion of the lower alkyl ester of cysteine or the mineral acid salt thereof in the aqueous solution is 3–10% by weight.

2. The composition for permanent waving of hair as claimed in claim 1 wherein the lower alkyl ester of cysteine is the methyl ester of cysteine.

3. The composition for permanent waving of hair as claimed in claim 1 wherein said mineral acid salt is the hydrochloride.

4. The composition for permanent waving of hair as claimed in claim 1 wherein the salt of the lower alkyl ester of cysteine is the hydrochloride of the methyl ester of cysteine.

5. The composition for permanent waving of hair as claimed in claim 1 wherein the pH of the aqueous solution is 6.5–7.5.

6. The composition for permanent waving of hair as claimed in claim 1 wherein the aqueous solution contains at least one additive selected from the group consisting of an effective amount of a penetrant, a stabilizing agent, a wetting agent, a viscosity-increasing agent, a perfume, a coloring agent, an emulsifier, and an antihistamine.

7. A composition for permanent waving of hair consisting essentially of an aqueous solution of a lower alkyl ester of cysteine or a mineral acid salt thereof and having a pH of 6.5–7.7, wherein the proportion of the lower alkyl ester of cysteine or the mineral acid salt thereof in the aqueous solution is 3–10% by weight, and at least one additive selected from the group consisting of an effective amount of a penetrant, a stabilizing agent, a wetting agent, a viscosity-increasing agent, a perfume, a coloring agent, an emulsifier, and an antihistamine, said stabilizing agent being an ethylenediaminetetraacetate.

8. The composition for permanent waving of hair as claimed in claim 7, wherein the pH of the aqueous solution is about pH 7.7.

9. A method of permanent waving of hair in a cold or hot system comprising applying a composition consisting essentially of an aqueous solution of a lower alkyl ester of cysteine or a mineral acid salt thereof and having a pH 6.5–7.7 , wherein the proportion of the lower alkyl ester of cysteine or the mineral acid salt thereof in the aqueous solution is 3–10% by weight to the hair; and then washing the hair.

* * * * *